US00PP23142P2

(12) United States Plant Patent
Danziger

(10) Patent No.: US PP23,142 P2
(45) Date of Patent: Oct. 23, 2012

(54) ***ARGYRANTHEMUM* PLANT NAMED 'DARGY31'**

(50) Latin Name: *Argyranthemum frutescens*
Varietal Denomination: DARGY31

(75) Inventor: Gavriel Danziger, Moshav Mishmar Hashiva (IL)

(73) Assignee: Danziger 'DAN' Flower Farm

( * ) Notice: Subject to any disclaimer, the term of this patent is extended or adjusted under 35 U.S.C. 154(b) by 0 days.

(21) Appl. No.: 13/134,681

(22) Filed: Jun. 13, 2011

(51) Int. Cl.
*A01H 5/00* (2006.01)

(52) U.S. Cl. ..... Plt./406

(58) Field of Classification Search ..... Plt./406
See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Argyranthemum* cultivar named 'DARGY31' is disclosed, characterized by abundant, early flowering and a yellow petal color. The new variety is a *Argyranthemum*, normally produced as an outdoor garden or container plant.

2 Drawing Sheets

Figure 1:
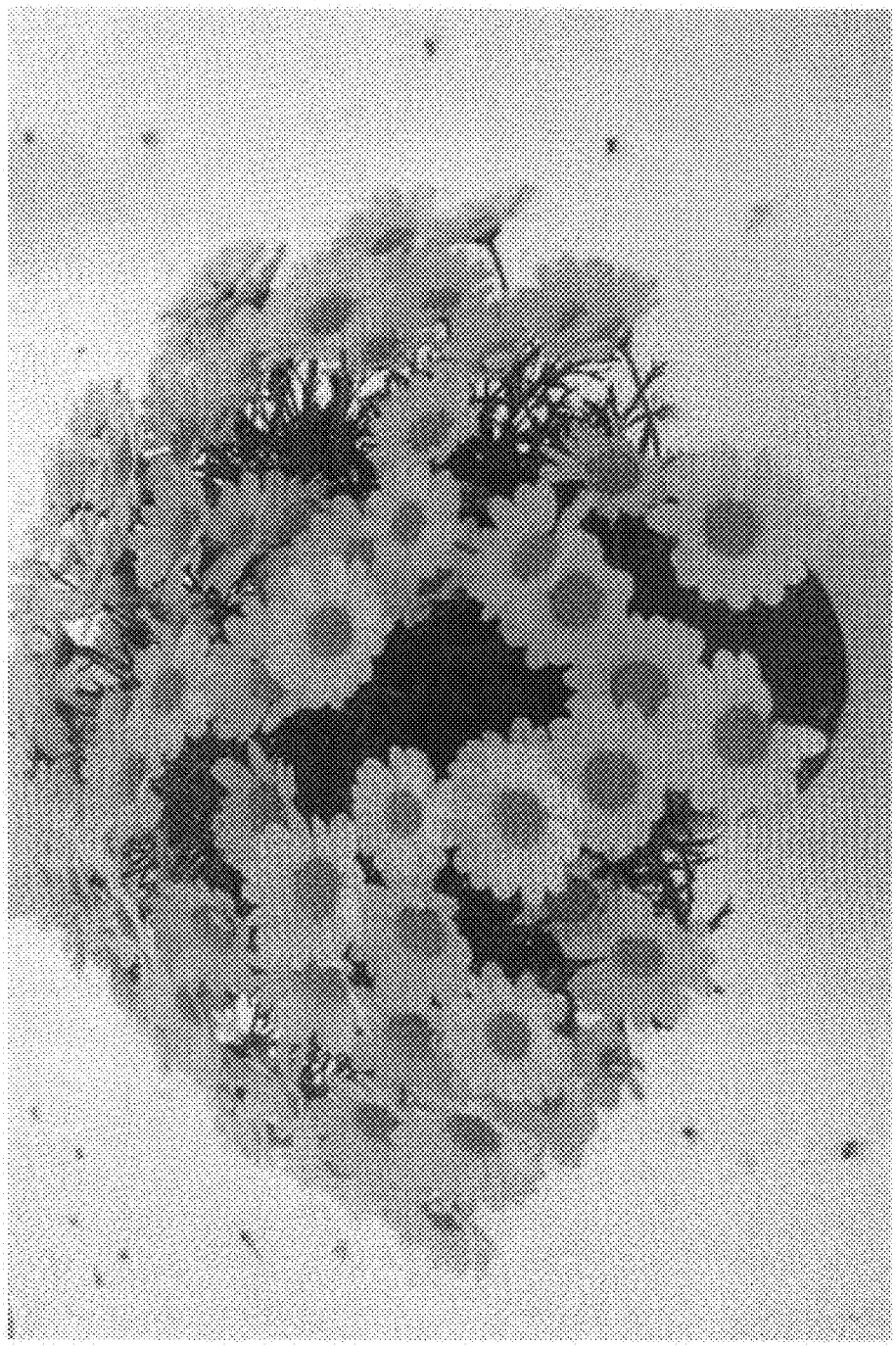

Latin name of the genus and species: *Argyranthemum frutescens*.

Variety denomination: 'DARGY31'.

BACKGROUND OF THE INVENTION

The new *Argyranthemum* cultivar is a product of a planned breeding program conducted by the inventor, Gavriel Danziger, in Moshav Mishmar Hashiva, Israel. The objective of the breeding program was to produce new *Argyranthemum* varieties for ornamental commercial applications. The cross resulting in this new variety was made during February 2008.

The seed parent is the unpatented, proprietary seedling variety referred to as *Argyranthemum frutescens* 'AR-0-12' The pollen parent is unknown, as the crossing resulting in 'DARGY31' was an open pollination, with unidentifiable pollen parents. The new variety was discovered in February 2009 by the inventor in a group of seedlings resulting from the 2008 crossing, in a research greenhouse in Moshav Mishmar Hashiva, Israel.

Asexual reproduction of the new cultivar 'DARGY31' by vegetative cuttings was first performed at a research greenhouse in Moshav Mishmar Hashiva, Israel in 2009 and has shown that the unique features of this cultivar are stable and reproduced true to type in successive generations.

SUMMARY OF THE INVENTION

The cultivar 'DARGY31' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DARGY31' These characteristics in combination distinguish 'DARGY31' as a new and distinct *Argyranthemum* cultivar:

1. More floriferous than similar *Argyranthemum* cultivars
2. Early flowering
3. Yellow petal color.

Plants of the new cultivar 'DARGY31' are similar to plants of the seed parent, *Argyranthemum frutescens* 'AR-0-12' in most horticultural characteristics, however, plants of the new cultivar 'DARGY31' have a denser plant habit, and flower earlier. Additionally, the new cultivar has larger flowers of a different color.

COMMERCIAL COMPARISON

Plants of the new cultivar 'DARGY31' are comparable to the commercial variety *Argyranthemum* 'DANARNEP' U.S. Plant Pat. No. 13,719. The *Argyranthemum* varieties are similar in most horticultural characteristics, however, plants of the new variety 'DARGY31' differ in having a denser, better branched growth habit and different color flowers. Additionally, the new variety is shorter, flowers earlier and has different foliage characteristics than 'DANARNEP'.

Plants of the new cultivar 'DARGY31' can also be compared to the commercial variety *Argyranthemum* 'Angelic Creamy Yellow' unpatented. The *Argyranthemum* varieties are similar in most horticultural characteristics, however, plants of the new variety 'DARGY31' are shorter, more compact and produce flowers with darker yellow petals. Additionally, the new variety is more densely branched, and produces flowers earlier than 'Angelic Creamy Yellow'.

BRIEF DESCRIPTION OF THE PHOTOGRAPHS

The accompanying photograph in FIG. 1 illustrates in full color a typical plant of 'DARGY31' grown in a greenhouse, in a 12 cm basket. Age of the plant photographed is approximately 12 weeks from a rooted cutting.

Figure 2:
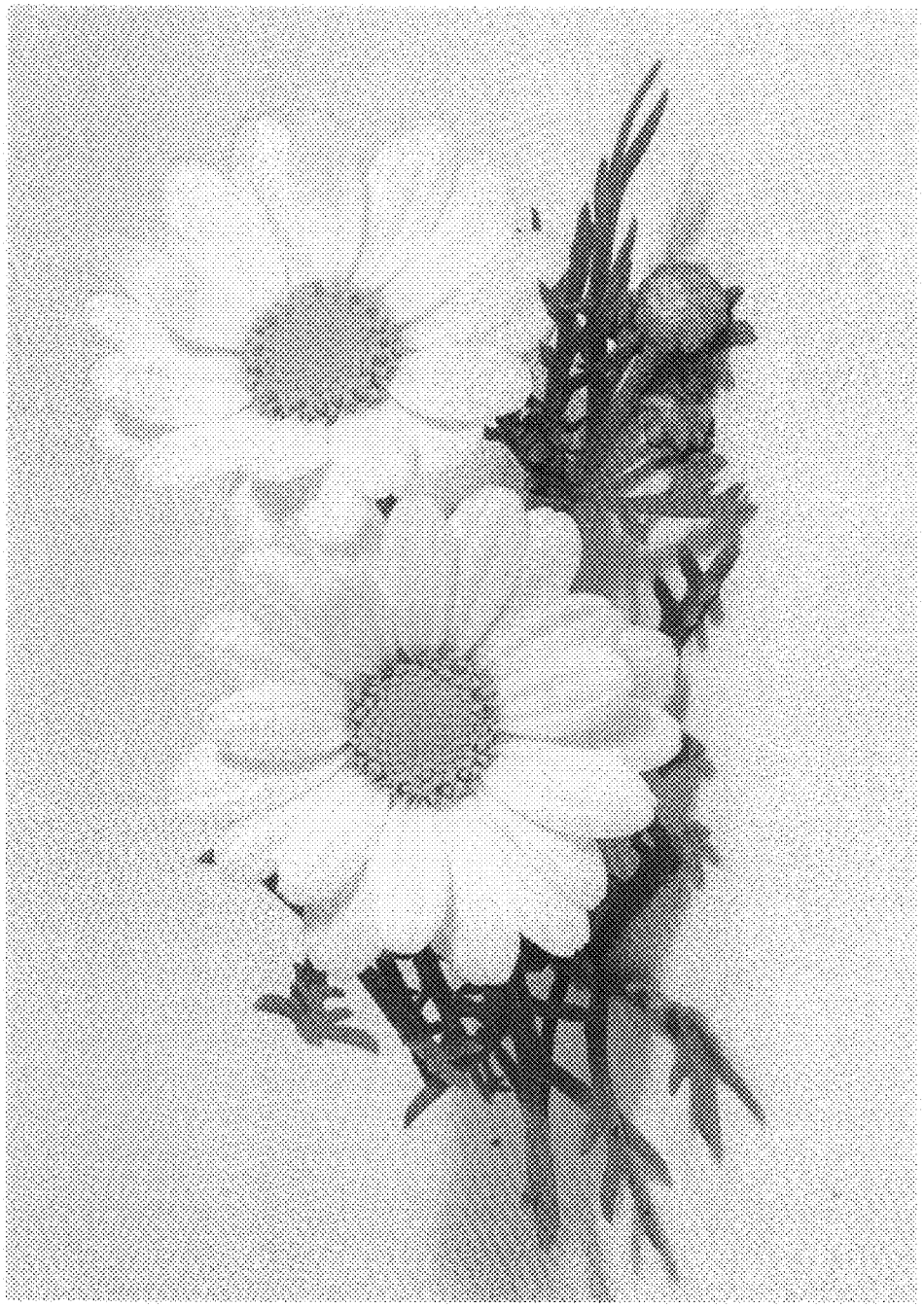

FIG. 2 illustrates in full color a close up of a typical bloom of 'DARGY31'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DARGY31' plants grown in a greenhouse during Winter in Mishmar Hashiva, Israel. The growing temperature ranged from 16° C. to 23° C. during the day and from 8° C. to 12° C. during the night. General light conditions are bright, normal sunlight. Measurements and numerical values represent averages of typical plant types.

Botanical classification: *Argyranthemum frutescens* 'DARGY31'.

PROPAGATION

Time to rooting: 14 days at approximately 20-25° C.

Root description: Fine, fibrous and white, RHS N999D in color.

PLANT

Pot size of plant described: 12 cm.

Age of plant described: Approximately 60 to 70 days.

Growth habit: Globular

Height: Approximately 30 cm to top of uppermost inflorescence.

Plant spread: Approximately 35 cm.

Growth rate: Rapid

Branching characteristics: Freely branching with lateral flowering branches forming at every node; dense and bushy.

Length of lateral branches: Approximately 10 cm.

Diameter of lateral branches: Approximately 0.3-0.5 cm.

Texture of lateral branches: Smooth.

Internode length: Approximately 4 cm.

Strength of stem: Above average.

Color of lateral branches: Green, RHS 138B.

Aspect/angle of branches: 30°-45°.

Number of leaves per lateral branch: Approximately 35-40.

FOLIAGE

Leaf:

*Arrangement*.—Alternate.

*Average length*.—Approximately 5.5-6 cm.

*Average width*.—Approximately 2 cm.

*Shape of blade*.—Pinnatipartite.

*Apex*.—Rounded.

*Base*.—Wedge-shaped.

*Attachment*.—Petiolate.

*Margin*.—Serrate.

*Texture of top surface*.—Slightly warty.

*Texture of bottom surface*.—Slightly warty.

*Appearance top surface*.—Matte.

*Appearance bottom surface*.—Matte.

*Leaf internode length*.—Approximately 0.5 cm.

*Color*.—Young foliage upper side: Green, RHS 137C. Young foliage under side: Green, RHS 137D. Mature foliage upper side: Green, RHS 137B. Mature foliage under side: Green, RHS 137C.

*Venation*.—Type: Parallel. Venation color upper side: Green, RHS 137C. Venation color under side: Green, RHS 137D.

Petiole: Length: 2.5 cm. Diameter: 0.2-0.3 cm. Pubescence: None. Color: Green, RHS 137C.

FLOWER

Natural flowering season: Spring/summer.

Individual flower longevity: Flowering of a single flower lasts about 20 days.

Quantity of flowers per plant: Approximately 80 open flowers and 20 buds when plant is in full bloom.

Bud:

*Bud shape*.—Round.

*Bud length*.—Approximately 0.5 cm.

*Bud diameter*.—Approximately 0.7-0.8 cm.

*Bud color*.—Apex: Greyed-green, RHS 197C, Base: Green, RHS 137D.

Inflorescence:

*Form*.—Single composite type daisy.

Flower:

*Diameter of entire flower*.—Approximately 4.5 cm.

*Depth of flower*.—Approximately 0.8 cm.

*Width of disc*.—Approximately 1.3 cm.

*Depth of disc*.—Approximately 0.6 cm.

Receptacle:

*Shape*.—Dome.

*Height*.—Approximately 0.9 cm.

*Diameter*.—Approximately 1.0 cm.

*Color*.—Apex: Near Green, RHS 137D.

Ray florets:

*Number of ray florets*.—Avg. About 20 to 22 in a single whorl.

*Length*.—Approximately 1.5-1.7 cm.

*Width*.—Approximately 0.7 cm.

*Shape*.—Lanceolate.

*Base*.—Attenuate.

*Apex shape*.—Rounded.

*Margin*.—Entire.

*Texture*.—Glabrous.

Color:

*Ray florets*.—Upper surface at first opening: Near RHS Yellow 4A. Upper surface at maturity: Near RHS Yellow 4A. Upper surface at fading: Near RHS Yellow 4C. Under surface at first opening: Near RHS Yellow 4C. Under surface at maturity: Near RHS Yellow 10D. Under surface at fading: Near RHS Yellow 10D.

*Disc florets*.—Number of Disc Florets:150-200. Length: Approximately 0.6 cm. Width: Approximately 0.1-0.15 cm. Shape: Bell-shaped, campanulate. Margin: Entire. At first opening: Near RHS Yellow-Orange 16B. At maturity: Near RHS Yellow Yellow-Orange 16B. At fading: Near RHS Yellow Yellow-Orange 16B.

Fragrance: Emits a strong fragrance when crushed.

PHYLLARIES

Number: Approximately About 15 to 17.

Arrangement: Tight double whorl.

Phyllary length: Approximately 0.2-0.3 cm.

Phyllary width: Approximately 0.1 cm.

Phyllary shape: Blunt deltoid.

Phyllary texture: Smooth.

Apex shape: Rounded.

Base shape: Obtuse.

Margin: Entire.

Color: Yellow-green, RHS 144C all surfaces.

Peduncle:

*Peduncle length*.—Approximately 6-6.5 cm.

*Peduncle diameter*.—Approximately 0.1-0.15 cm.

*Angle*.—Approximately 45°-90° from center of whorl.

*Color*.—Yellow-green, RHS 146B.

*Peduncle texture*.—Smooth.

REPRODUCTIVE ORGANS

Disc florets:

*Androecium*.—Stamens: 5 (fused as tube). Anther shape: Basifixed. Anther length: Approximately 0.08-0.1 cm. Anther color: Yellow, RHS 13A. Pollen quantity: Abundant. Pollen color: Yellow, RHS 9B.

*Gynoecium*.—Pistil number: 150-200. Pistil shape: Terete. Pistil length: Approx. 0.05 cm. Style length: Approx. 0.02 cm. Style color: Yellow, RHS 12B. Stigma shape: Stringy. Stigma color: Yellow, RHS 12B. Ovary diameter: 0.7 cm. Ovary color : Yellow-green, RHS 149 D.

Ray florets:

*Androecium*.—Stamens: About 20 to 22 arranged in one to two whorls. Anther shape: linear. Anther length: Approximately About 1.5 cm. Anther color: Yellow, RHS 13A. Pollen quantity: Abundant. Pollen color: Yellow, RHS 13A.

*Gynoecium*.—Pistil number: 20-22. Pistil length: Approx. 0.05 cm. Style length: Approx. 0.02 cm. Style color: Close to 150C. Stigma shape: Two-parted. Stigma color: Close to Yellow-Green 151C. Ovary diameter: about 0.05 cm. Ovary color: Close to Green-White 157D.

OTHER CHARACTERISTICS

Seeds and fruits: Few produced.

*Shape*.—Oblong.

*Color*.—Greyed-yellow, RHS 161A.

*Size*.—Length about 0.2 cm Width about 0.1 cm.

Disease/pest resistance: Neither resistance nor susceptibility to normal diseases and pests of *Argyranthemum* has been observed.

Various tolerance: Plants of the new *Argyranthemum* have exhibited good tolerance to drought, rain and wind. Flowering may cease during hot periods (temperatures above 35° C.). Low temperature tolerance to 10° C.

What is claimed is:

1. A new and distinct cultivar of *Argyranthemum* plant named 'DARGY31' as herein illustrated and described.

* * * * *